United States Patent [19]

Barberet et al.

[11] Patent Number: Plant 6,209

[45] Date of Patent: Jun. 21, 1988

[54] CARNATION NAMED LONPINDI

[75] Inventors: Nicole Barberet; Yves Ducloux, both of Antibes, France

[73] Assignee: Laboratoire de Physiologie Vegetale de la Londe, La Londe, France

[21] Appl. No.: 872,242

[22] Filed: Jun. 9, 1986

[51] Int. Cl.[4] ..... A01H 5/00

[52] U.S. Cl. ..... Plt./70

[58] Field of Search ..... Plt./70–73

*Primary Examiner*—James R. Feyrer

*Attorney, Agent, or Firm*—Charles W. Rummler; W. Dennis Drehkoff

[57] ABSTRACT

A new variety of carnation plant particularly distinguished by the substantially white coloration of its medium sized blooms which are borne singly on relatively long stems of erect and rigid character, its vigorous and upright growth habit, abundant foliage, and its resistance to *Fusarium oxysporum.*

1 Drawing Sheet

BACKGROUND OF THE NEW PLANT

This new carnation cultivar originated as a sport of the variety "Londorga" (U.S. Plant Pat. No. 5,784) being grown at 83250 La Londe, Les Maures, France, this sport having been discovered in 1982 and propagated by us with cuttings for testing and evaluation because of its unusual yellowish white color and its red striations at the petal tips. This initial propagation appeared to be so satisfactory that continued propagation through successive generations, by both cuttings and in vitro procedures, demonstrated conclusively that the new plant retained all of the distinguishing characteristics of the original natural mutation and that these characteristics hold true from generation to generation and appear to be firmly fixed.

DESCRIPTION OF THE DRAWING

This new carnation cultivar is illustrated by the accompanying photographic drawing which shows a three-fourths top view of a group of flowers in several stages of maturity, the color rendition being as nearly true as it is reasonably possible to obtain by conventional photographic procedures.

DESCRIPTION OF THE NEW PLANT

The following is a detailed description of our new carnation cultivar based upon observation of plants grown in Southern France during the current year, the color designations being according to The R.H.S. Colour Chart published by The Royal Horticultural Society of London, England.

THE PLANT

Origin: Natural mutation.

Parentage: Cultivar "Londorga" (U.S. Plant Pat. No. 5,784).

Classification:

*Botanic.*—*Dianthus caryophyllus.*

*Commercial.*—Standard Carnation.

Form: Bush having at least four erect stems emitted near the ground.

Height: 125 cm., in average, at about eight months.

Main stem:

*Length.*—Less than 15 cm. due to pinching.

Growth: Vigorous, upright and rigid.

Branching character: Average, with stems to a height of about 125 cm.

Foliage:

*Quantity.*—Abundant.

*Number of leaves.*—More than 120.

*Leaf size.*—About 14 cm. long and 1.4 cm. wide (in average) at the seventh node.

*Leaf shape.*—Oblong with rolled margin.

*Texture.*—Leathery.

*Color.*—Upper side — 189B. Under side — 189A.

*Ribs and veins.*—Hardly noticeable.

*Rachis.*—Hardly noticeable.

*Leaflets.*—None.

THE BUD

Size: Medium.

*Diameter.*—About 2 cm.

*Length.*—About 3.7 cm.

Form: Short ovoid, nearly cylindrical.

Rate of opening: Normal.

Color of petals:

*When sepals first divide and petals begin to unfurl-*.—Same as at full bloom (4D).

Sepals:

*Number.*—Unusually five.

*Shape.*—Joined together at the lower part and generally deltoid with sharp points at the tips. The sepals are hooded over the bud until the bud begins to break and when the flowers open the sepals curl back.

*Color.*—Outside — 137D and 145B. Inside — 145C.

*Striae.*—Longitudinal.

Calyx:

*Shape.*—Almost cylindrical but widening toward the top.

*Size.*—Medium large, long and of medium width.

*Splitting.*—Sometimes the calyx splits.

*Aspect.*—Smooth.

Flower stem:

*Length.*—About 65 cm. (in average).

*Character.*—Erect and rigid.

*Color.*—145C and 189B.

THE FLOWER

Blooming habit: Recurrent, blooming profusely in spring and fall, with a tendency to give few blooms in late fall.

Size of bloom: Medium.
*Diameter.*—About 9 cm. (in average).
*Depth.*—About 5.5 cm. (in average).
Borne: Singly on a rigid and upright stem.
Shape: High centered when bloom first opens; becoming dome-shaped as the bloom matures.
Petalage:
*Number of petals: About* 50 (in average).
*Arrangement.*—Imbricated.
*Shape.*—Fan-shaped with rounded and not very serrated margins.
*Texture.*—Soft.
*Appearance.*—Satiny.
*Color.*—Outer petals: Upper side, 4D with tip end striations of 48B. Base, yellowish green. Reverse side, 4D and 48C. Inside petals: Body, 4D and 48B. Base, yellowish green. Reverse side, 4D and 48C.
Petaloids: Rarely present.
*Size.*—Smaller than the petals.
*Color.*—The same as the petals.
Flower stem:
*Length.*—About 65 cm., cut at tenth node.
*Character.*—Upright and of good strength.
*Color.*—189B.
Fragrance: Slight.
Discoloration after full bloom: Weak.
Persistence: The petals hang on and dry.
Disease resistance: Resistant to *Fusarium oxysporum* as observed I.N.R.A. Antibes-France.
Lasting quality:

*As cut flower.*—At least ten days in vase keeping.

REPRODUCTIVE ORGANS

Stamens:
*Number.*—15, arranged around the ovary.
Anthers: Less than 4 mm. in length.
*Color.*—Whitish.
Filaments:
*Length.*—About 1.5 cm. (in average).
*Color.*—Whitish.
Pistils:
*Number.*—2 to 4.
Styles:
*Length.*—About 1.5 cm. (in average).
*Color.*—Greenish white.
Stigmas:
*Color.*—Yellowish white.
Character of ovaries: Ribbed.

In general, the characteristics of this plant may be more-or-less strongly modulated according to environmental conditions, method of cultivation, and latitude where grown. In general, this new carnation cultivar is similar to the variety "Londorga" but has a yellowish white color and is red striated at its outer end margin.

We claim:

1. A new and distinct carnation plant, substantially as herein shown and described, characterized by its yellowish white color and red striated margins at the outer ends of the petals.

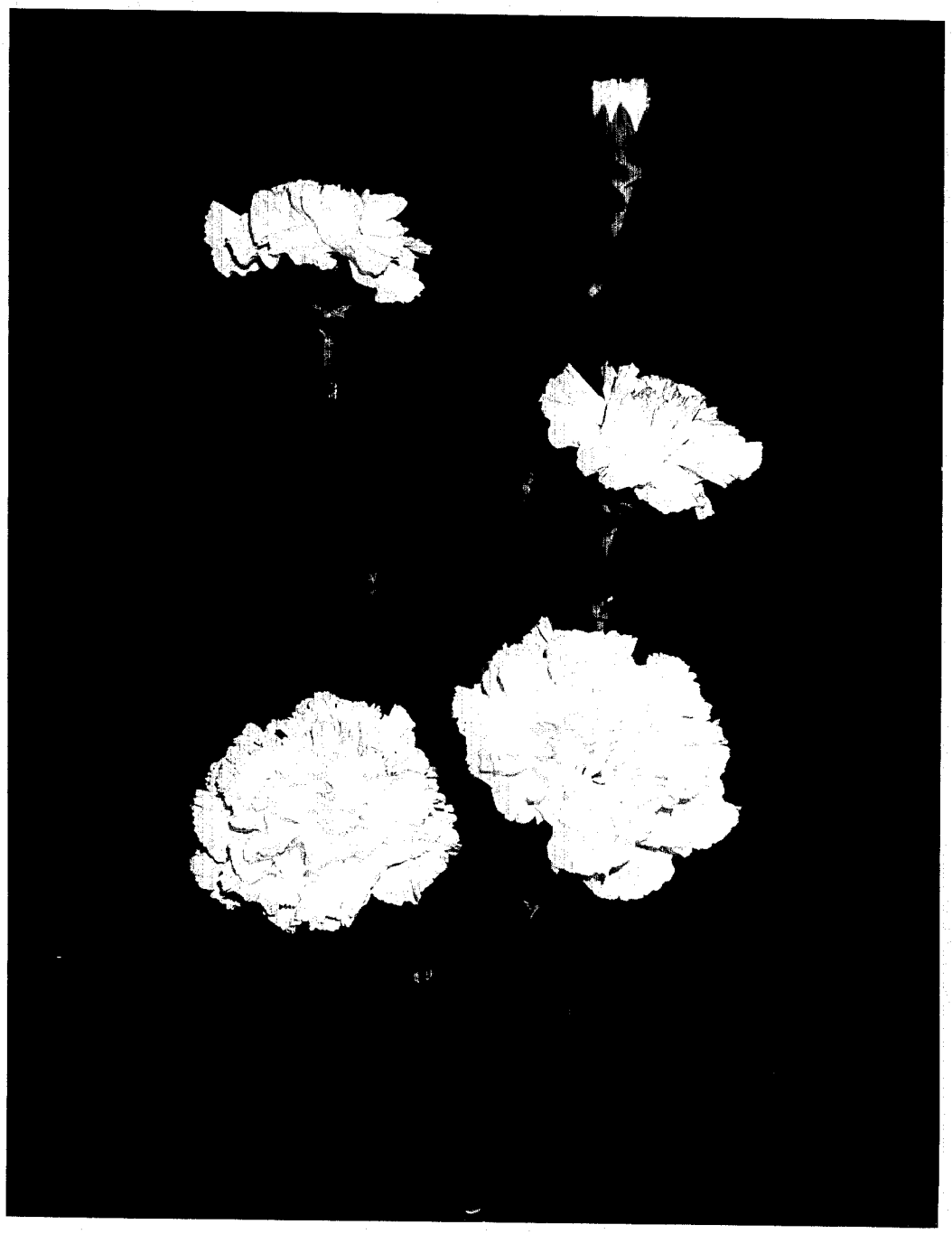

* * * * *